United States Patent
Imai

[11] Patent Number: 5,426,978
[45] Date of Patent: Jun. 27, 1995

[54] NON-DESTRUCTIVE AXLE FLAW DETECTING APPARATUS

[75] Inventor: Yukio Imai, Kanagawa, Japan

[73] Assignee: Mitsubishi Denki Kabushiki Kaisha, Tokyo, Japan

[21] Appl. No.: 132,505

[22] Filed: Oct. 5, 1993

[30] Foreign Application Priority Data

Oct. 9, 1992 [JP] Japan .................. 4-271646

[51] Int. Cl.⁶ ............................. G01N 29/04
[52] U.S. Cl. .......................... 73/622; 73/597; 367/99
[58] Field of Search ............... 73/622, 636, 597, 598, 73/611, 634, 644, 602, 609, 628, 632; 367/99; 340/674, 675; 364/506, 507

[56] References Cited

U.S. PATENT DOCUMENTS

| | | |
|---|---|---|
| 3,044,291 | 7/1962 | Klatchko . |
| 3,685,350 | 8/1972 | Pettinato . |
| 4,229,796 | 10/1980 | Garrett .................. 73/622 |
| 4,235,112 | 11/1980 | Kaiser .................... 73/634 |
| 4,254,660 | 3/1981 | Prause .................... 73/622 |
| 4,699,007 | 10/1987 | Kawashima et al. ........ 73/622 |
| 4,700,572 | 10/1987 | Senba et al. ............. 73/622 |
| 4,800,757 | 1/1989 | Hashinoki et al. ......... 73/597 |
| 4,991,441 | 2/1991 | Nottingham et al. ....... 73/634 |
| 5,174,155 | 12/1992 | Sugimoto ................. 73/622 |

FOREIGN PATENT DOCUMENTS 0000259 1/1979 European Pat. Off. .
8711532 U 11/1987 Germany .

OTHER PUBLICATIONS

Handbook of Non-Destructive Inspection, Nikkan Kogyo Shinbun-sha Apr. 28, 1978, pp. 480-482 & 494-495.

Primary Examiner—Hezron E. Williams
Assistant Examiner—Helen C. Kwok
Attorney, Agent, or Firm—Wolf, Greenfield & Sacks

[57] ABSTRACT

The flaw detecting apparatus comprises a sensor head including a first sensor for detecting the center of the center hole and a second sensor for detecting a flaw. A driver moves the sensor head along a first line passing through the center hole and then along a second line passing through the center of the center hole and perpendicular to the first line, thereby placing the sensor head at a position facing the center hole, on the basis of the output of the first sensor. Subsequently, the driver rotates the sensor head to a predetermined position where a flaw is detected, on the basis of the output of the second sensor.

16 Claims, 10 Drawing Sheets

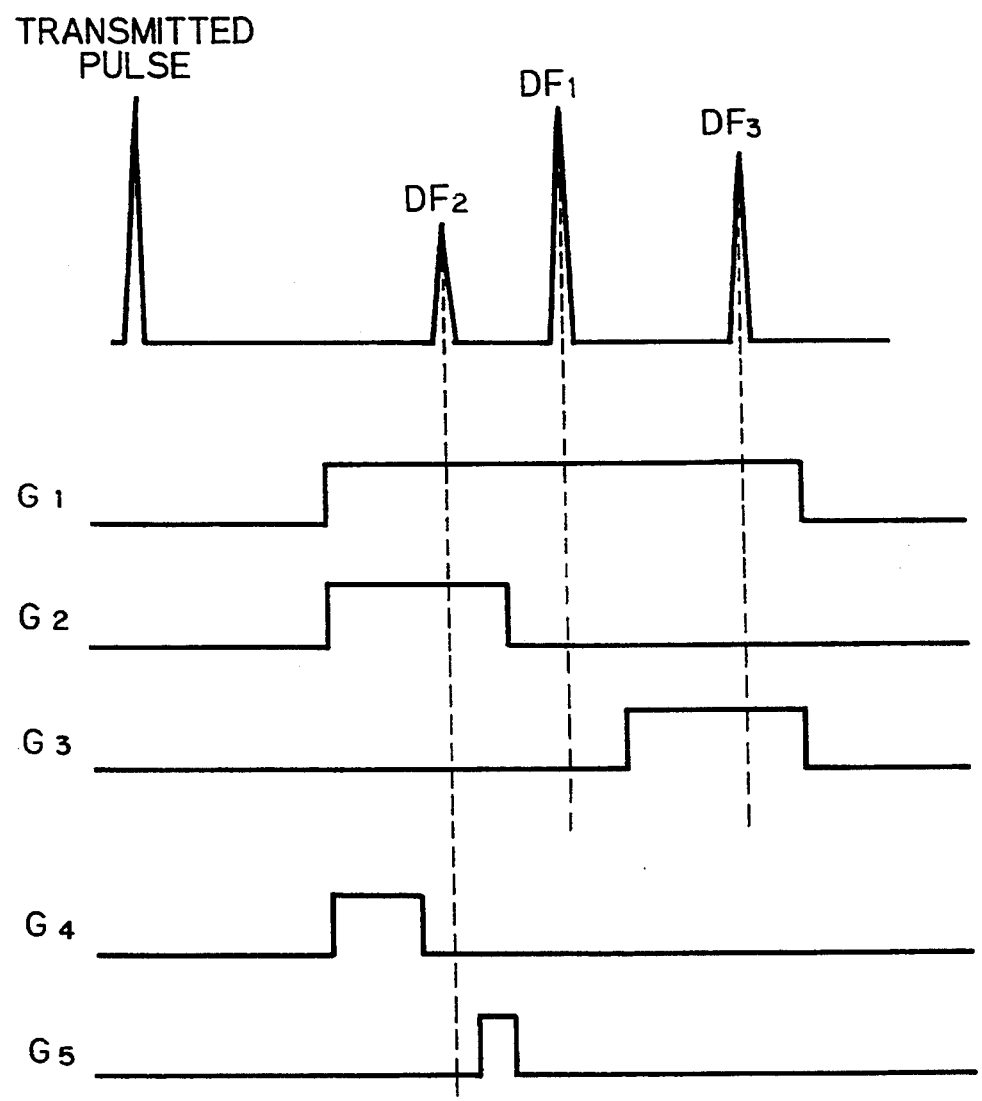

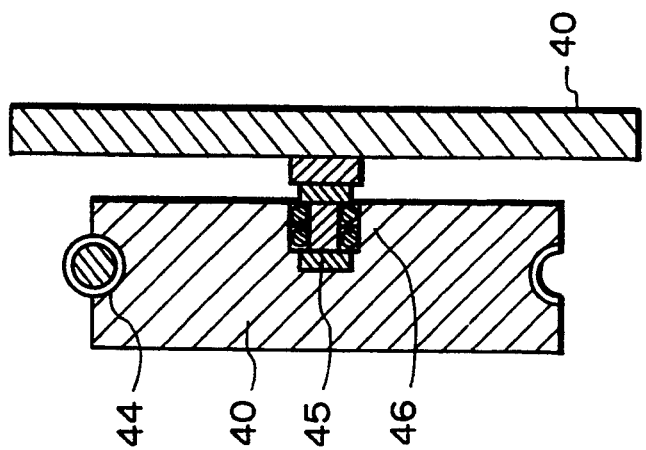
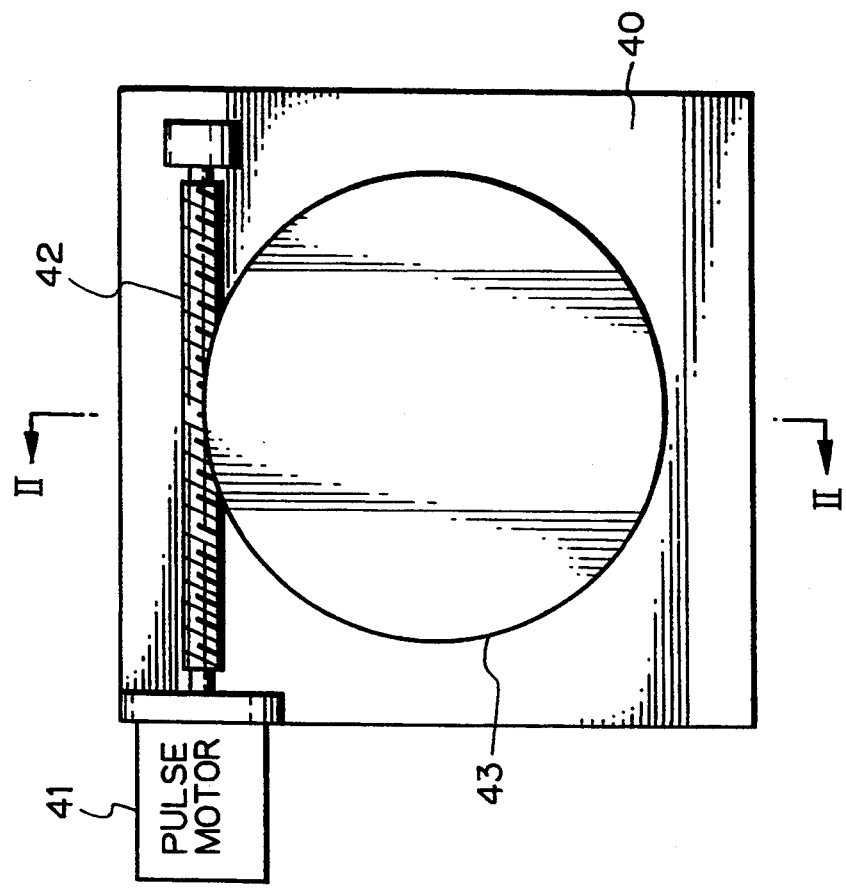

NON-DESTRUCTIVE AXLE FLAW DETECTING APPARATUS

BACKGROUND OF THE INVENTION

1. Field of the Invention

The present invention relates to a flaw detecting apparatus for conducting non-destructive flaw inspection for axles, such as an axle of electric railcars.

2. Related Arts

FIG. 1 is a schematic diagram showing the structure of an axle ultrasonic flaw detecting apparatus of the prior art. In this figure, the reference numeral 1 designates an axle of an electric railcar as an inspected object; 3a, 3b drivers for moving and shifting probe heads 2a, 2b in mutually vertical three directions; 4 an ultrasonic flaw detector which is provided to cause the probe heads 2a, 2b to transmit an ultrasonic wave and receive echoes inputted to the probes 2a, 2b; 5 a display unit for displaying the output of the ultrasonic flaw detector 4; 6 an oil feeding unit for filling a gap between the probe heads 2a, 2b and the end faces of the axle 1 with oil; 7 an operation controller for outputting operation instructions to the drivers 3a, 3b and oil feeding unit 6.

FIGS. 2(a) and 2(b) show an enlarged view of an end of the axle 1 of an electric railcar, more specifically FIG. 2(a) is a side elevation of the axle 1, while FIG. 2(b) is a plan view of one end face of the axle 1. In these figures, $N_0$ designated a center hole for positioning a wheel lathe used to cut a wheel at its center and $N_1$, $N_2$, $N_3$ threaded holes which receive bosses for mounting the wheel to the axle 1 and which are arranged at an angular interval of 120°; and $N_4$ a marking for indicating a wheel number.

When a switch of the operation controller 7 for moving the probe head 2a in a first direction is depressed in order to set the probe head 2a in contact with one end face of the axle 1, a control signal is sent to the driver 3a from the operation controller 7 and the probe head 2a is moved in the first direction by the driver 3a. Similar to the moving in the first direction, the probe head 2a can also be moved in the second and third directions by the driver 3a in response to the depression of the 2nd and 3rd direction buttons provided on the operation controller 7. Upon completion of the operations explained above, the probe head 2a comes into contact with the center of one end face of the axle 1. The probe head 2b can also come in contact with the center of the other end face of the axle 1 in the same manner as mentioned above. After the probe heads 2a, 2b have come in contact with the centers of both end faces of the axle 1, oil is instructed to be fed by the operation controller 7. When an instruction to feed oil is issued, a control signal is sent to the oil feeding unit 6 from the operation controller 7 and the gaps between the end faces of the axle 1 and the probe heads 2a, 2b are respectively filled with oil. Next, the ultrasonic flaw detector 4 is operated to transmit an ultrasonic wave from a probe built in the probe head 2a and echoes are received by the probe built in the probe head 2a and then transmitted through the ultrasonic flaw detector 4 to the display 5 which displays the echoes as shown in FIGS. 3(a) and 3(b).

FIG. 3(a) shows a typical waveform in the case the axle 1 does not contain any flaw, while FIG. 3(b) shows a typical waveform in the case flaws exist inside the axle 1. In those figures, S designates a surface echo; B a bottom echo; F a flaw echo and H a step echo.

Next, when a switch of the operation controller 7 for rotating the probe head 2a is depressed, a control signal is sent to the driver 3a from the operation controller 7 and the driver 3a rotates the probe head 2a. During the rotation of the head 2a, an operator monitors waveforms displayed on the display 5 and stops the rotation of the probe head 2a by operating the operation controller 7 when a flaw waveform as shown in FIG. 3(b) which is different from a standard waveform shown in FIG. 3(a) appears. When the probe head 2a stops, the amplitude of each echo is evaluated to determine whether it should be considered to emanate from a flaw or not on the basis of a waveform displayed on the display 5. When an echo is determined to be generated by a flaw, the distance from one end face of the axle 1 to the flaw is obtained using the waveform on the display 5 and is then recorded. A circumferential position of the flaw is also recorded as an angular position relative to the threaded hole $N_2$ located in the right of the marking $N_4$ shown in FIG. 2(b).

When the probe head 2a passes over the threaded holes $N_1$, $N_2$ and $N_3$ formed on one end face of the axle 1, a displayed waveform is disturbed and flaw detection is not carried out for such regions.

Using the driver 3b and probe head 2b, flaw detection is also carried out for the other end face of the axle 1.

Since a flaw detecting apparatus of the prior art is constituted such as explained above, an operator is required to manually position a probe head so that it comes into contact with the center of an end face of an axle. This gives rise to a problem that a positioning accuracy considerably fluctuates and that a long time is required for such positioning.

Moreover, since a result of flaw detection is visually judged in addition to manually positioning a probe head, reproducibility in the result of flaw detection may be compromised if the same axle is Inspected a plurality of times. Visual judgment also results in a drawback that a skilled operator is essential.

SUMMARY OF THE INVENTION

A general object of the present invention is to provide a non-destructive flaw detecting apparatus which can overcome such drawbacks of the prior art as explained above.

It is another object of the present invention to provide a non-destructive flaw detecting apparatus which realized automatic flaw detection.

It is other object of the present invention to provide a non-destructive flaw detecting apparatus which ensures excellent reproducibility in the result of flaw detection and requires no skilled operator in determining the existence of flaws.

In order to achieve such objects, a preferred embodiment of a flaw detecting apparatus of the present invention comprises: a sensor head having (1) a first sensor provided corresponding to a center hole formed on an end face of an axle to detect the center of the end face, (2) a second sensor provided corresponding to an axle fitting hole at a predetermined position relative to the first sensor to detect a flaw, and (3) a third sensor provided corresponding to a marking formed on the end face at a predetermined position relative to the first and second sensors to detect the marking; a drive means for driving the sensor head so that the first sensor moves along first and second straight lines which pass through the center of the end face and cross with each other and that the second and third sensors rotate around the center of the end face; an arithmetic means including (1) a means for obtaining an intersecting point of the first and the second straight lines on the basis of a signal level obtained by the first sensor when the first sensor moves along the first straight line, (2) a means for obtaining the center of the end face on the basis of a signal level obtained by the first sensor when the first sensor moves along the second straight line, (3) a means for obtaining the center of the axle fitting hole on the basis of a signal level obtained by the second sensor when the sensor head is rotated and passes over said axle fitting hole while the first sensor is located at the center of the end face and the sensor head is in contact with the end face and for detecting the marking from a signal obtained by the third sensor to obtain an angle formed between the marking and the center of the axle fitting hole, and (4) a means for obtaining the true origin of the axle fitting hole from the center of the axle fitting hole and the obtained angle; a storage means for storing the center of the axle fitting hole as a temporary origin for starting flaw detection and for storing the true origin; a control means for controlling the drive means in response to the outputs of the arithmetic means and storage means; and a processing means for processing output signals from the first, second and third sensors.

The flaw detector explained above initially sets a flaw detection gate which includes the entire flaw detection range and detects a maximum echo within this gate. Then, the gate is set narrower to include one side and then the other side of the initial gate relative to a detected maximum echo and maximum echoes are detected in the respective gates. In this manner, the gate is sequentially divided into two subgates for maximum echo detection.

As explained heretofore, according to the present invention, since the sensor head is brought into contact with the end face of the axle by automatically detecting the center of a center hole provided at the end face of the axle, positioning accuracy of the sensor head can be raised and a time required for positioning the sensor head can be curtailed.

Moreover, since threaded holes provided concentrically around the center hole of the end face of the axle and the indicator for representing axle information can be detected, automatic inspection of the end face of the axle can be realized.

In addition, since flaw detection can be carried out through automatic evaluation by sequentially detecting flaws from the largest a flaw detection time can be shortened and reproducibility of a flaw detection result can be improved.

BRIEF DESCRIPTION OF THE DRAWINGS

FIG. 2(a) is a plan view of an end face of the axle 1 shown in FIG. 1, while

FIG. 3(a) shows ultrasonic echoes displayed on the display unit shown in FIG. 1 when no flaw is detected in the axle 1, while

FIG. 11 explains how gates are set during the flaw detection with the flaw detecting apparatus shown in FIG. 4;

FIG. 13(a) is a plan view of a driving unit for rotating a probe head, and FIG. 13(b) is a cross section thereof taken along a line II—II in FIG. 13(a).

DESCRIPTION OF THE PREFERRED EMBODIMENTS

Figure 1:
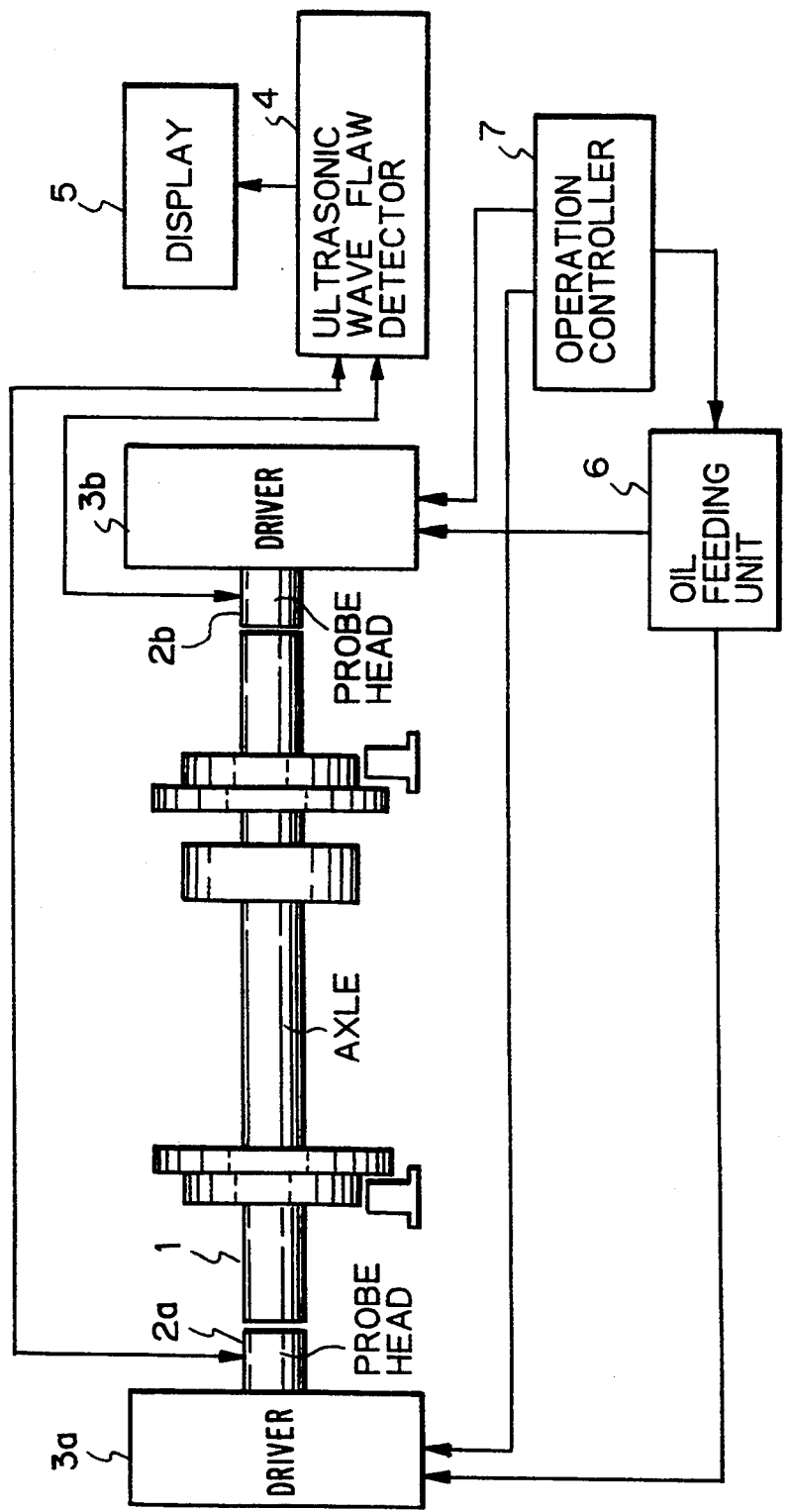
FIG. 1 is a schematic diagram illustrating the structure of an ultrasonic axle flaw detecting apparatus of the prior art.
Figure 2A:
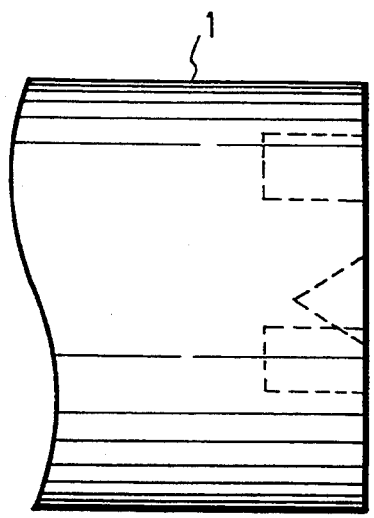
Figure 2B:
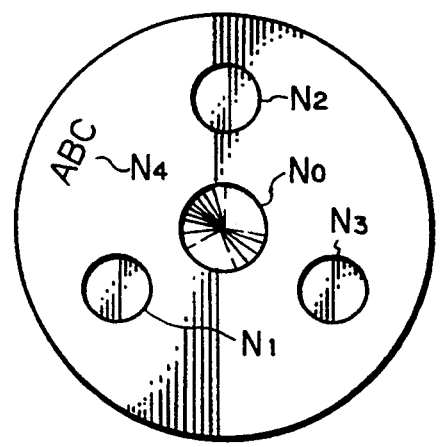
FIG. 2(b) is an enlarged diagram of the end face of the axle 1.
Figure 3A:
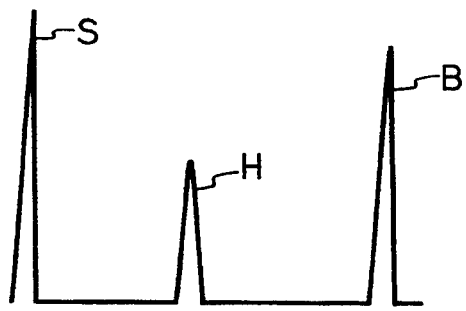
Figure 3B:
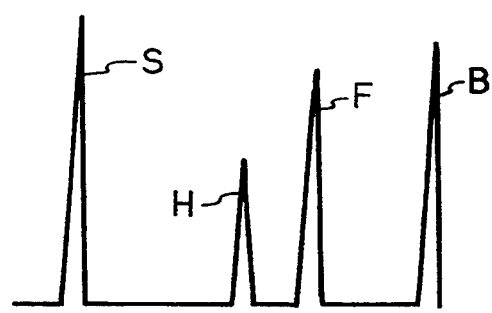
FIG. 3(b) shows ultrasonic echoes when a flaw is detected in the axle 1.
Figure 4:
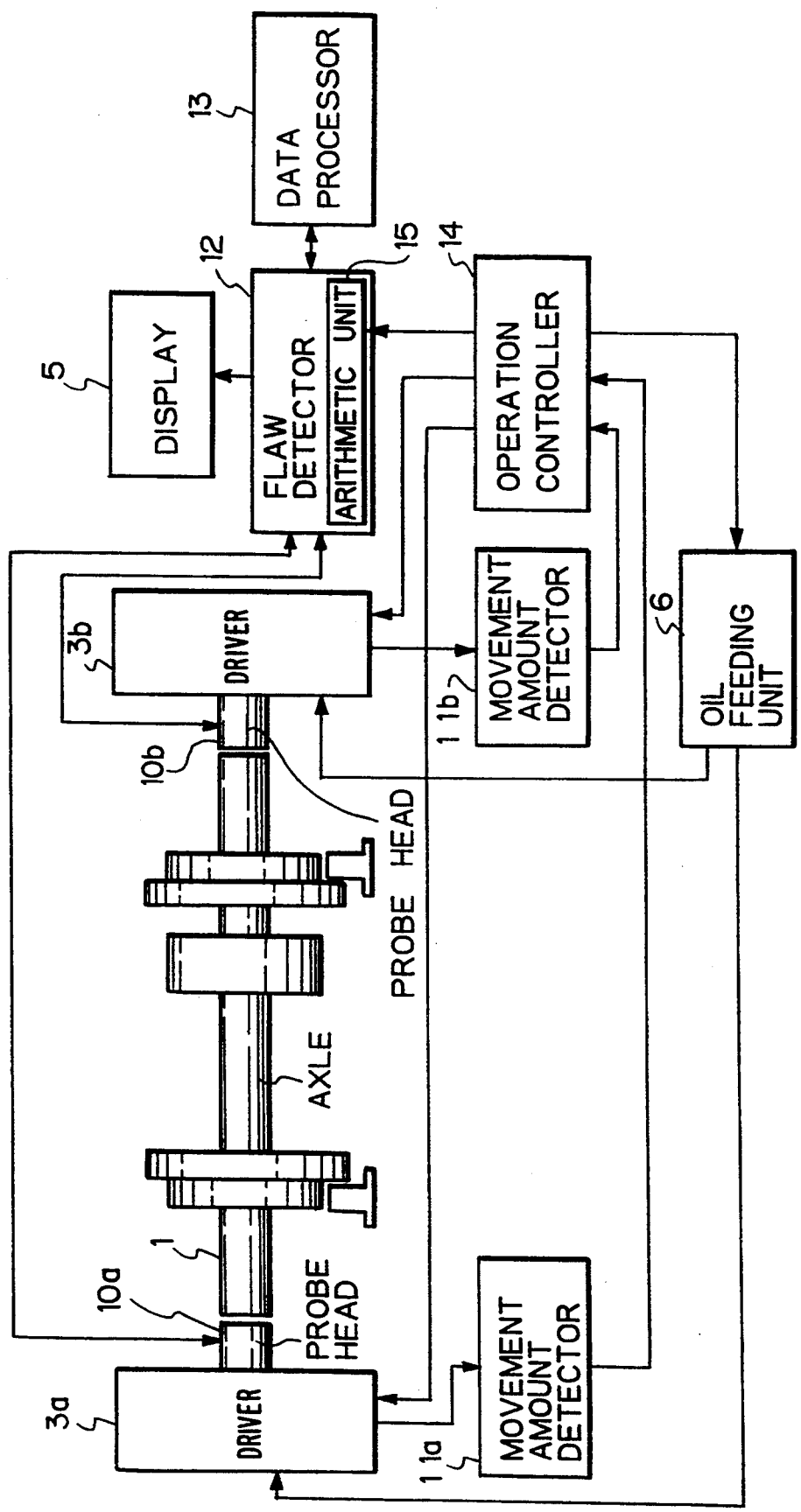
FIG. 4 is a schematic diagram illustrating the structure of an ultrasonic axle flaw detecting apparatus to which the present invention is applied.

FIG. 4 is a diagram illustrating an embodiment of an axle flaw detecting apparatus of the present invention. In this figure, structural elements are the same as and similar to those in FIGS. 1 to 3 are designated by the same reference numerals. Numerals 10a, 10b designate probe heads each having first and second probes for transmitting and receiving ultrasonic waves, a distance measuring probe and a displacement sensor; 11a, 11b movement amount detectors for detecting amounts of movement of the probe heads 10a, 10b; 12 an ultrasonic flaw detector which causes the first and second probes and the distance measuring probe provided in the probe heads 10a, 10b to transmit ultrasonic waves and receive echoes reflected by flaws as well as receiving data from the displacement sensor; 13 a data processor for receiving flaw detecting data from the ultrasonic flaw detector 12, causing such data to be displayed as a graph or printed out on a recording sheet and setting a variety of parameters such as a length of the axle 1 and gate positions in the ultrasonic flaw detector 12; 14 an operation controller for sending operation instructions to the drivers 3a, 3b and the oil feeding unit 6 and receiving amounts of movement of the probe heads 10a, 10b from the movement amount detectors 11a, 11b; 15 an arithmetic unit which receives the amounts of movement detected by the movement amount detectors 11a, 11b from the operation controller 14 to compute amounts of return of the probe heads 10a, 10b for the drivers 3a, 3b.

Figure 5:
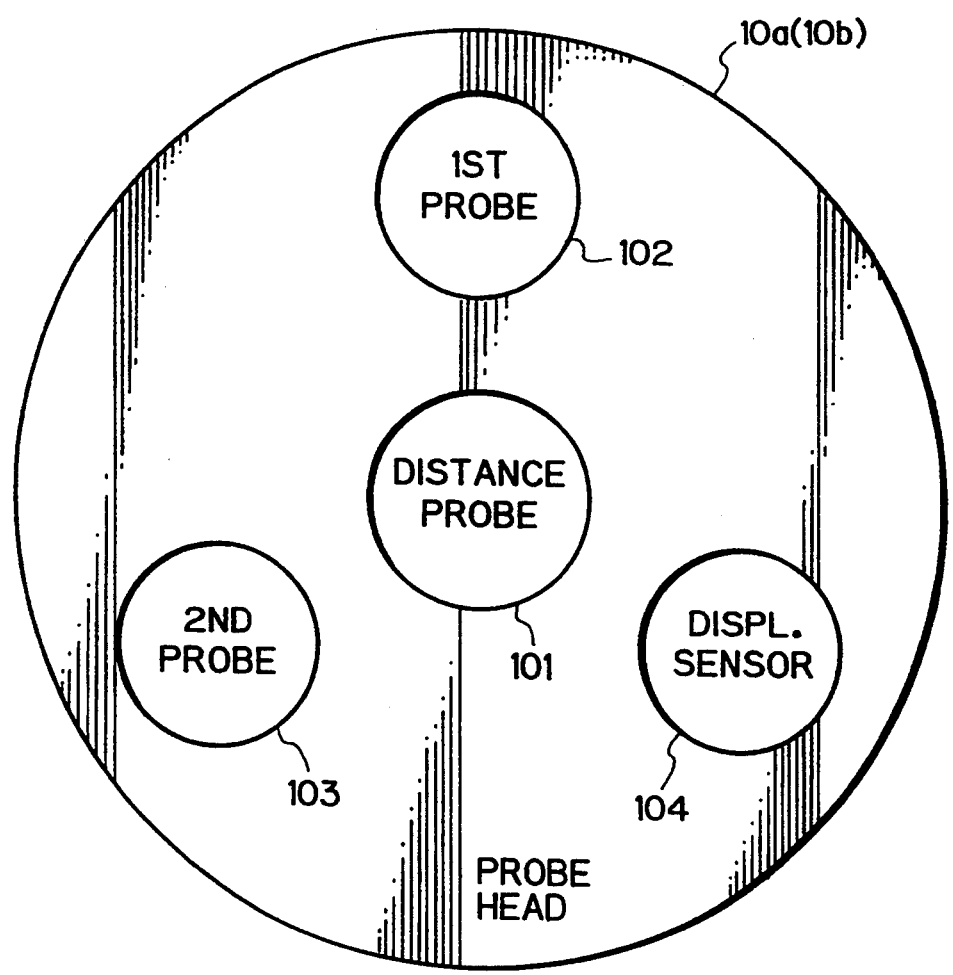
FIG. 5 shows the arrangement of probes and a sensor provided in a probe head shown in FIG. 4.

FIG. 5 shows details of the structure of each probe head 10a or 10b. As shown in this figure, the probe head 10a (10b) comprises a distance measuring probe 101 for measuring a distance between the probe head 10a (10b) and one end face of the axle 1 to detect the center hole $N_0$ (FIG. 2(b)), a first probe 102 for conducting a vertical flaw detection to detect the threaded holes $N_1$, $N_2$, $N_3$, a second probe 103 for conducting an oblique flaw detection and a displacement sensor 104 for detecting a marking $N_4$.

The probes 101–103 and the displacement sensor 104 are provided at predetermined positions respectively corresponding to the center hole $N_0$, threaded holes $N_1$, $N_2$, $N_3$ and the marking $N_4$ formed at one end face of the axle 1. More specifically, the distance measuring probe 101 is provided on the probe head 10a (10b) opposed to the center hole $N_0$, while the first probe 102, second probe 103 and displacement sensor 104 are respectively provided at an angle of 120 degrees from each other on a circle, at the center of which the distance measuring probe 101 is located.

Operations of the apparatus shown in FIG. 4 will be explained with reference to a flowchart shown in FIG. 6.

In this figure, a variety of parameters such as the length of axle I to be measured and gate positions required for flaw detection are set in the data processor 13 in a step 21. Upon completion of the setting of the parameters, the data processor 13 transfers such preset data to the ultrasonic flaw detector 12, resulting in the setting of the ultrasonic flaw detector 12 in a flaw detection start waiting condition. It is noted that the probe head 10a is prepositioned at a position a predetermined distance from one end face of the axle 1 along a straight line $L_1$ (FIG. 7) passing an area near the center of the center hole $N_0$.

Figure 7:
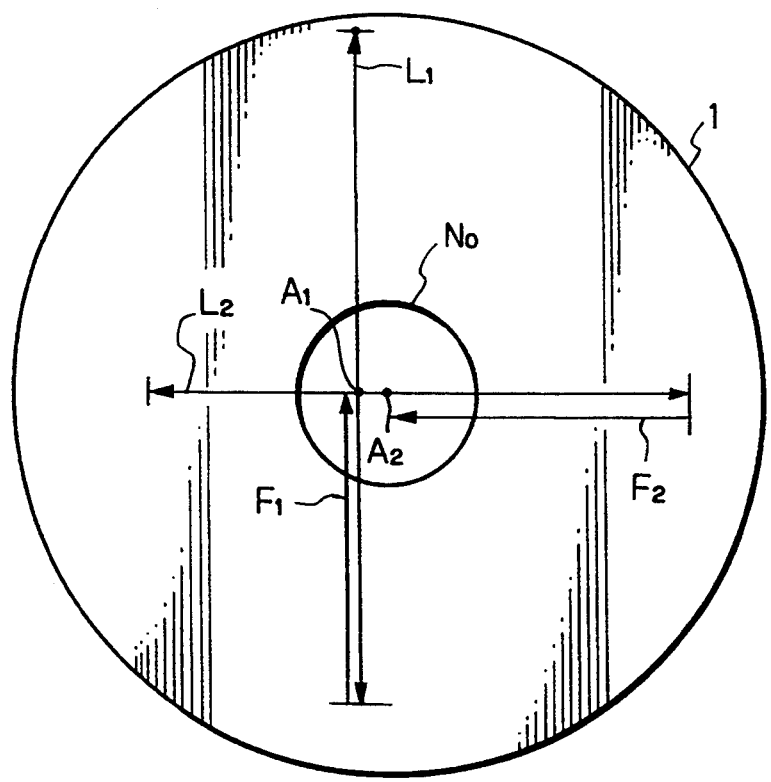
FIG. 7 shows paths of movement of the probe head for the purpose of detecting a center hole with the flaw detecting apparatus shown in FIG. 4.

In a step 22, when an operator depresses a flaw detection start switch of the operation controller 14, the operation controller 14 outputs an operation instruction to the driver 3a to initially move the probe head 10a toward the center hole $N_0$ along the straight line $L_1$ as shown in FIG. 7, in order to detect the center hole $N_0$ of the axle 1.

At the same time as the probe head 10a starts to move, the operation controller 14 outputs a distance measurement start signal to the ultrasonic flaw detector 12, which causes the distance measuring probe 101 to transmit the ultrasonic wave and receive echoes. An amount of movement of the probe head 10a in the direction of a straight line $L_1$ is detected by the movement amount detector 11a and is then transferred to the arithmetic unit 15 through the operation controller 14. The flaw detector 12 records the echoes received from the distance measuring probe 101 for every movement of a predetermined distance, while moving the probe head 10a along the straight line $L_1$. When the probe head 10a has moved to the position where the echo along the straight line $L_1$ is minimized, the operation controller 14 outputs a stop instruction to the driver 3a and a distance measurement terminate signal to the flaw detector 12. As a result, the probe head 10a stops at the center point of the center hole $N_0$. This process will be explained hereunder in detail.

The arithmetic unit 15 obtains a center position $A_1$ along the straight line $L_1$ on one end face of the axle 1, that is, an intersection point of the straight line $L_1$ and a straight line $L_2$ which orthogonally crosses the straight line $L_1$ and passes a center point $A_2$ of the center hole $N_0$, on the basis of the amplitude of echoes measured by the ultrasonic flaw detector 12 every time the probe head 10a moves a predetermined distance and a moving distance of the distance measuring probe 101 between the movement start and stop positions, and then computes a distance $F_1$ between the stop position of the probe head 10a and the center position $A_1$ to output a computed result to the operation controller 14. The operation controller 14 then outputs the distance $F_1$ to the driver 3a to cause the probe head 10a to return to the center point $A_1$ along the straight line $L_1$.

Figure 8:
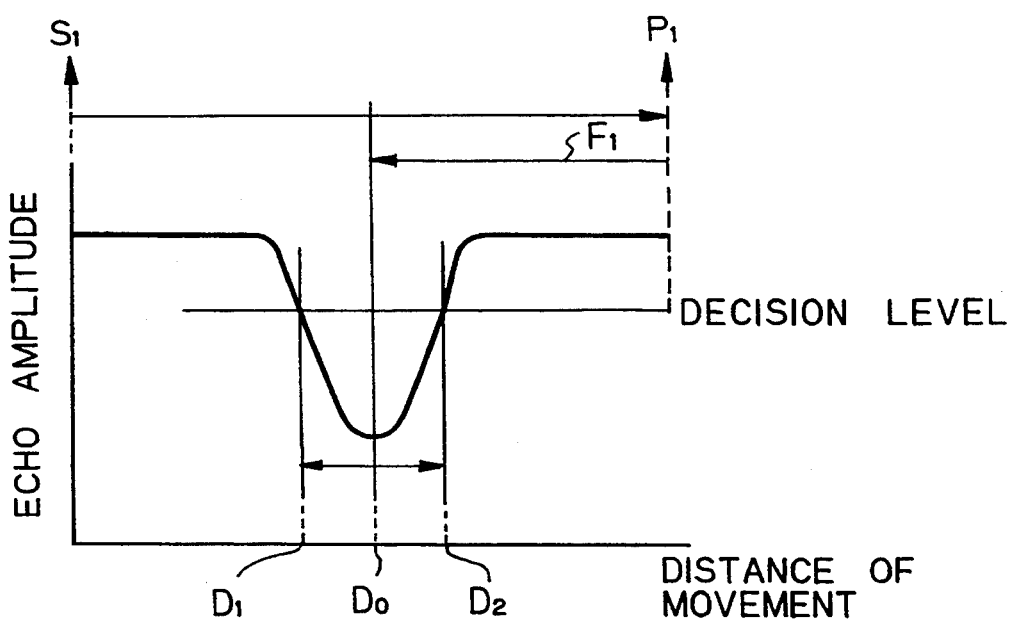
FIG. 8 explains how to detect the center hole with the flaw detecting apparatus shown in FIG. 4.

A method for obtaining the center point $A_1$ will then be explained with reference to FIG. 8. In this figure, a horizontal axis shows a distance of movement, $S_1P_1$ of the probe head 10a inputted to the arithmetic unit 15, while a vertical axis shows the amplitude of echoes inputted from the distance measuring probe 101 to the ultrasonic flaw detector 12. An echo amplitude is high and stable when the probe 101 is located outside of the center hole $N_0$ because the end face of the axle 1 is flat. When the probe 101 passes over the center hole $N_0$, a level of the echo is decreased because the center hole $N_0$ has an oblique side wall as shown in FIG. 2(a). The arithmetic unit 15 obtains a distance at a point $D_1$ where the level of echo becomes smaller than a predetermined decision level and a distance at a point $D_2$ where the echo level becomes larger than the decision level and then obtains the center point $A_1$ between the point $D_1$ and $D_2$ based on those distances.

The arithmetic unit 15 further obtains a distance from the stop position $P_1$ of the probe head 10a to the point $A_1$, namely, an amount of return $F_1$, and then outputs such an amount to the operation controller 14. The operation controller 14, responding to the output of the arithmetic unit 15, moves the probe head 10a along the straight line $L_1$ so that the probe 101 is positioned at the center point $A_1$, and thereafter, moves the probe head 10a to a movement start position of the second straight line $L_2$. Then, the operation of the probe head 10a to move from a movement start position to a stop position on the second straight line $L_2$ and to return to the center point $A_2$ from the stop position along the straight line $L_2$ is carried out in the same manner as that carried out along the straight line $L_1$, enabling the probe head 10a to position at the center point $A_2$ of the end face, that is, the operation controller outputs a distance $F_2$ to the driver 3a to cause the probe head 10a to return to the center point $A_2$ along straight line $L_2$. After the probe head 10a has positioned at the center position $A_2$, the operation controller 14 instructs the driver 3a to move the probe head 10a until it comes in contact with the end face of the axle 1 and stop the probe head 10a. The distance of movement of the probe head 10a is equal to the distance from the probe head 10a to the end face of the axle 1 and can be obtained by the ultrasonic flaw detector 12 from the echo received by the distance measuring probe 101.

Figure 6:
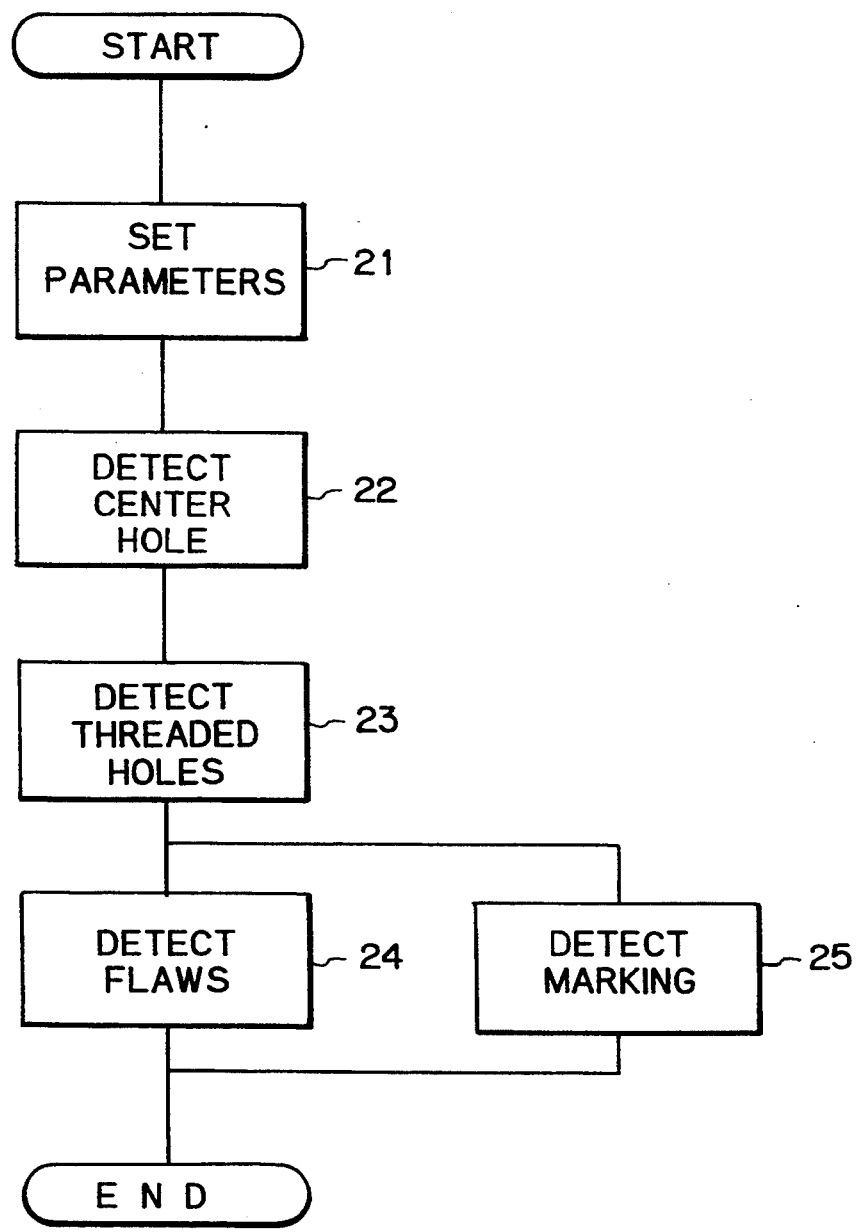
FIG. 6 is a flowchart for explaining operations of a flaw detecting apparatus shown in FIG. 4.

When the probe head 10a comes in contact with the end face of the axle 1 and stops the movement, a step for detecting the threaded holes $N_1-N_3$ is executed in a step 23 of FIG. 6. This step will be explained next in detail.

Figure 9:
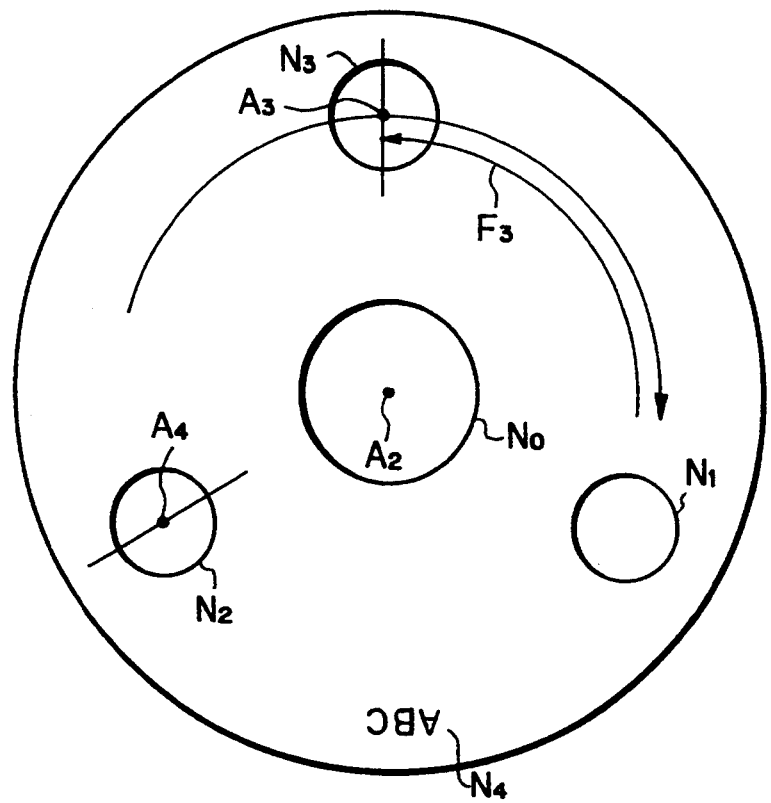
FIG. 9 shows paths of rotation of the probe head for the purpose of detecting the center of a threaded hole with the flaw detecting apparatus shown in FIG. 4.

First, when the operation controller 14 issues an oil feed instruction signal to the oil feeding unit 6, the gap between the end face of the axle 1 and the probe head 10a is filled with oil through the driver 3a and probe head 10a. After a specified period of time has passed, the operation controller 14 instructs the driver 3a to rotate the probe head 10a and the driver 3a rotates the probe head 10a clockwise around the center point $A_2$, as shown in FIG. 9. Upon starting of rotation of the probe head 10a, the operation controller 14 outputs a flaw detection start signal to the ultrasonic flaw detector 12 to cause the detector 12 to transmit an ultrasonic wave from the first probe 102 and receive echoes.

An amount of rotation of the probe head 10a is detected by the movement amount detector 11a and then supplied via the operation controller 14 to the arithmetic unit 15.

The ultrasonic flaw detector 12 records the echoes (bottom surface echoes) received from the first probe 102 for every specified angle of rotation of the probe head 10a. Since an angular interval between adjacent two of the threaded holes $N_1$, $N_2$ and $N_3$ is 120 degrees, the operation controller 14 rotates the probe head 10a a predetermined angle (for example, 15 degrees) sufficient to detect one of the threaded holes (threaded hole $N_3$ in the case shown in FIG. 9). When the probe head 10a rotates the predetermined angle, the operation controller 14 outputs a stop instruction to the driver 3a to stop the probe head 10a and a flaw detection terminate signal to the ultrasonic flaw detector 12. The arithmetic unit 15 obtains the center point $A_3$ of the threaded hole $N_3$ over which the first probe 102 has passed on the basis of echo amplitudes measured by the ultrasonic flaw detector 12 for every rotation of the probe head 10a by the predetermined angle, computes an amount of return (angle) $F_3$ of the probe head 10a from the stop position to the center point $A_3$ of the threaded hole $N_3$ and outputs a computed result to the operation controller 14. The operation controller 14 outputs such an amount of return $F_3$ to the driver 3a which in turn moves the probe head 10a to the center point $A_3$ of the threaded hole $N_3$.

Figure 10:
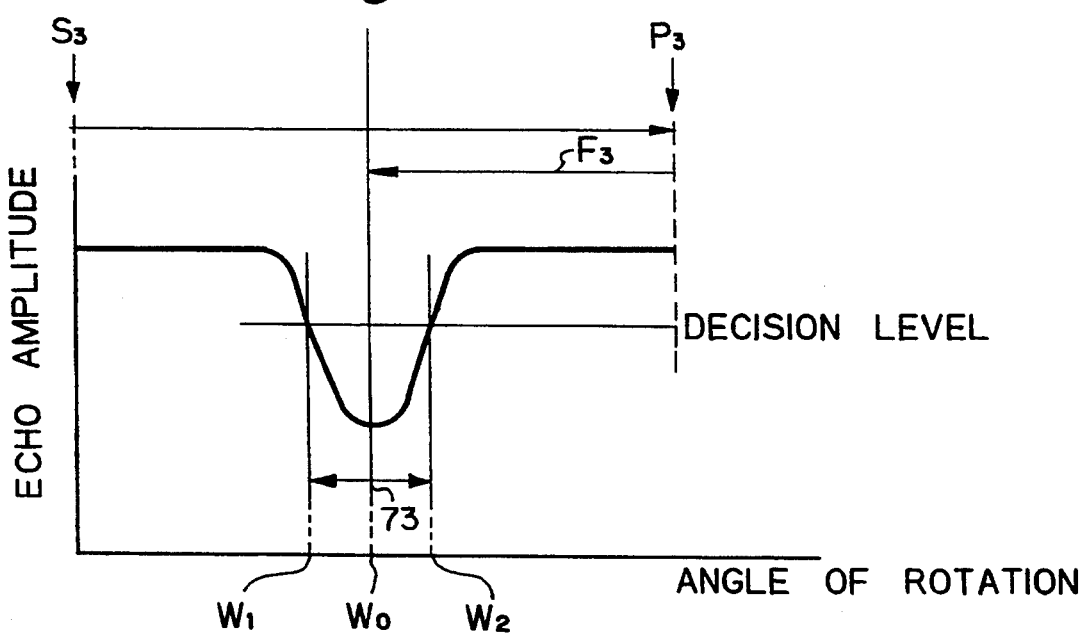
FIG. 10 explains how to detect the center hole with the flaw detecting apparatus shown in FIG. 4.

A method of obtaining the center point $A_3$ of the threaded hole $N_3$ will be explained with reference to FIG. 10. In FIG. 10, a horizontal axis shows an angle of rotation $S_3$, $P_3$ of the probe head 10a inputted to the arithmetic unit 15, while a vertical axis the amplitude of echoes received by the probe 102 and inputted to the ultrasonic flaw detector 12 for every angle of rotation. The echo amplitude is stable at a higher level since the end face of the axle 1 is flat when the probe 102 is located outside the threaded holes $N_1$, $N_2$, $N_3$. When the probe 102 passes over any one of the threaded holes $N_1$, $N_2$, $N_3$ no ultrasonic wave travels within the axle 1 and an echo level is lowered because each threaded hole makes a cavity as shown in FIG. 2(a).

The arithmetic unit 15 computes a total angle of rotation of the probe head 10a from the start $S_3$ to the time when an echo level becomes lower than a predetermined decision level. Specifically, the arithmetic unit 15 obtains an angle $W_1$ when the echo level becomes smaller than the decision level and an angle $W_2$ when the echo level becomes larger than the decision level and thereby obtains a center angle $W_0$ between these angels $W_1$, $W_2$. The angular difference between $W_1$, and $W_2$ is represented by reference numeral 73. The arithmetic unit 15 also obtains an angle $P_3$ between the position where the probe head 10a stops and the position $A_3$ corresponding to the angle $W_0$, namely, an amount of return $F_3$ which is outputted to the operation controller 14.

The operation controller 14 and the ultrasonic flaw detector 12 store the position of the center $A_3$ of the threaded hole $N_3$ over which the probe head 10a stops as a temporary origin for starting flaw detection. Subsequently, since threaded holes similar to those $N_1$-$N_3$ are also provided at the other end face of axle 1, the operation controller 14 issues an instruction to the driver 3b to locate the probe head 10b to the position corresponding to the temporary origin $A_3$.

When the probe heads 10a, 10b stop at the temporary origins, the operation controller 14 starts flaw detection in a step 34 (FIG. 6). Specifically, the operation controller 14 outputs rotation instructions to the drivers 3a, 3b and the drivers 3a, 3b respectively rotate the probe heads 10a, 10b a predetermined angle (for example, 30 degrees). When the probe heads 10a, 10b rotate the predetermined angle and stop, the operation controller 14 outputs a flaw detection start signal to the ultrasonic flaw detector 12 which then starts flaw detection responsive to the flaw detection start signal.

The flaw detecting operation conducted by the flaw detecting apparatus shown in FIG. 4 will be explained with reference to FIG. 11. As shown in FIG. 11, the ultrasonic flaw detector 12 sets a first flaw detection gate $G_1$ to include the entire flaw detection range. Next, the ultrasonic flaw detector 12 detects a flaw $DF_1$ producing the maximum echo in the preset gate $G_1$ and then stores a distance of the flaw $DF_1$ in the axial direction from one end face of the axle 1 and an angular position of the flaw $DF_1$. Next, the flaw detector 12 sets a second flaw detection gate $G_2$ to include either side of the flaw detection gate $G_1$ relative to the flaw $DF_1$, detects a flaw $DF_2$ producing the maximum echo in the gate $G_2$ and stores axial and angular positions of the flaw $DF_2$ in a manner similar to the case of the flaw $DF_1$. Next, the ultrasonic flaw detector 12 sets a flaw detection gate $G_3$ to include the remaining side of the flaw detection gate $G_1$ relative to the flaw $DF_1$, detects a flaw $DF_3$ producing the maximum echo in the gate $G_3$ and stores axial and angular positions of the flaw $DF_3$. In the same manner, the flaw detection gate is sequentially narrowed the maximum echo in each narrowed gate (e.g. $G_4$, $G_5$) is detected and axial and angular positions of the flaws producing the maximum echoes are stored. When a predetermined number of flaws have been detected or an echo amplitude from a flaw becomes lower than a predetermined level, the ultrasonic flaw detector 12 outputs a flaw detection interrupt signal to the operation controller 14. During this period, the first probe 102 and the second probe 103 respectively execute flaw detecting operations sequentially. In the case where the probe 102 or 103 is located on any of the threaded holes, flaw detection is not carried out but an angular position of the threaded hole is stored.

The operation controller 14 outputs rotation instructions to the drivers 3a, 3b responsive to the flaw detection interrupt signal from the ultrasonic flaw detector 12 and rotates the probe heads 10a, 10b the predetermined angle. When the probe heads 10a, 10b are rotated respectively the predetermined angle and then stopped by the drivers 3a, 3b, a flaw detection gate is set to enable flaw detection. Thereafter, when flaw detection is completed at all predetermined circumferential position by repeating similar operations, the operation controller 14 outputs a flaw detection terminate signal to the ultrasonic flaw detector 12 and a control signal to the drivers 3a, 3b to return the probe heads 10a, 10b to the position of origin (point $A_4$ in FIG. 9). Simultaneously, the operation controller 14 outputs an oil feed stop signal to the oil feeding unit 6 to stop oil-feeding. The ultrasonic flaw detector 12 transfers stored flaw detection data to the data processor 13 responsive to the flaw detection terminate signal. As shown in FIG. 6, a step 25 for detecting the marking $N_4$ is carried out in parallel with the step 24 of flaw detection. While the probe head 10a is rotating, the displacement sensor 104 measures a size to detect the marking $N_4$ printed on the end face of the axle 1 based on the result of measurement so as to detect an angle $\theta$ between the temporary origin $A_3$ and the marking $N_4$. With the angle $\theta$ and the angle formed by adjacent two threaded holes, the center $A_4$ of the threaded hole $N_2$ next to the marking $N_4$ is set as the true origin and transferred to the data processor 13 together with flaw detection results. The true origin is set because the same flaw detection is performed regardless of an angular position of the axle 1 to realize good reproducibility of flaw detection. The data processor 13 displays flaw detection results inputted from the ultrasonic flaw detector 12 as a graph and prints out the results.

Figure 12B:
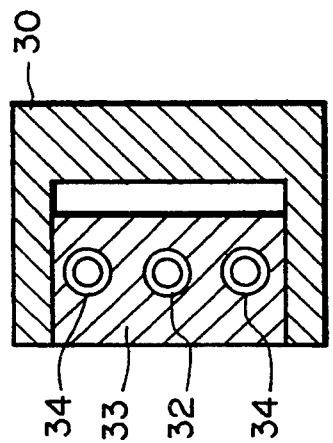
FIG. 12(b) is a cross section thereof taken along a line I—I in FIG. 12(a)
Figure 12A:
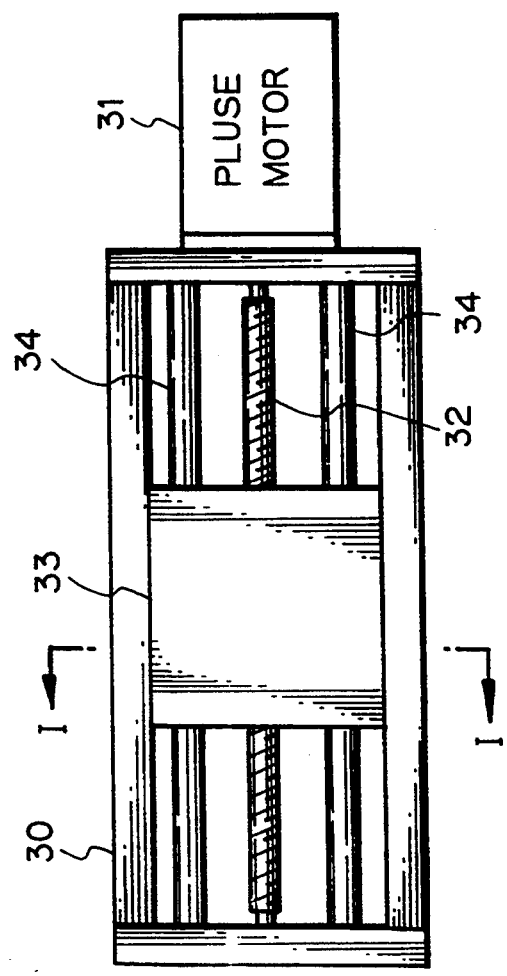
FIG. 12(a) is a plan view of a driving unit for shifting a probe head along one direction.

Turning to FIGS. 12(a) and 12(b) there is shown an example of a driving unit 3a1 for moving probe head 10a in one of the mutually vertical three directions. Driving unit 3a1 has a base plate 30, a pulse motor 31 mounted to one side wall of base plate 30 and operable to rotate in response to the number of pulses inputted to the pulse motor, a ball screw 32 rotatably supported between two opposite side walls of base plate 30 and rotated by pulse motor 31, a moving table 33 linearly moved by the rotation of ball screw 32, and guide axles 34 for guiding table 33. Ball bearings are provided between moving table 33 and guide axles 34, and the rotation of ball screw 32 is converted to linear movement of moving table 33 by ball screws (bearings) mounted to moving table 33.

In order to move probe head 10a along the one direction, operation controller 14 feeds pulses to pulse motor 31, the number of the pulses corresponding to the distance that moving table 33 is to be moved. In response to the fed pulses, pulse motor 31 rotates ball screw 32 at angles corresponding to the number of the fed pulses. The rotation of ball screw 32 moves table 33 linearly along guide axles 34, thereby shifting probe head 10a by a desired distance.

It is noted that driver 3a is equipped with two other driving units similar to driving unit 3a1 for the purpose of shifting probe head 10a in the remaining two directions, and that driver 3b has the same structure as driver 3a.

Turning to FIGS. 13(a) and 13(b), there is shown an example of a driving unit 3a2 for rotating probe head 10a. Driving unit 3a2 has a base plate 40, a pulse motor 41 mounted to one side of base plate 40 to rotate in response to the number of pulses inputted to the pulse motor, a worm gear 42 rotated by pulse motor 41, a rotating table 43 rotated by worm gear 42, a worm wheel 44 for transmitting the rotation of worm gear 42 to rotating table 43, an axle 45 for rotatably mounting table 43, and a bearing 46 provided between base plate 40 and rotating table 43.

In order to rotate probe head 10a, operation controller 14 feeds pulses to pulse motor 41, the number of the fed pulses corresponding to the angle that rotating table 40 is to be rotated. In response to the fed pulses, pulse motor 41 rotates worm gear 42 at angles corresponding to the number of the fed pulses. The rotation of worm gear 42 serves to rotate rotating table 41 through worm wheel 44, thereby rotating probe head 10a at a desired angle.

In the above embodiment, an apparatus for detecting flaws of axles of an electric railcar using an ultrasonic wave has been explained, but the present invention can also be applied to an axle other than that of an electric railcar and it is possible to use an X-ray or a neutron beam instead of an ultrasonic wave.

Moreover, in the embodiment, the center hole $N_0$, threaded holes $N_1$-$N_3$ and marking $N_4$ are formed on both end faces of an axle, but it is needless to say that the present invention can be applied to an axle having only the center hole $N_0$ or an axle having the center hole $N_0$ and threaded holes $N_1$-$N_3$.

In addition, in the embodiment, a distance measuring probe, first and second probes and a displacement sensor are used, but the present invention is not limited to such a structure.

Furthermore, it is also possible that an indicator such as a marking provided on an end face of an axle to indicate axle information may be read by, for example, an image pickup means for management of flaw detection data obtained from each axle.

What is claimed is:

1. A flaw detecting apparatus for non-destructively detecting a flaw in an axle, the axle having an end face which has a center hole, the flaw detecting apparatus comprising:
    a sensor head including a first sensor for detecting a center of the end face and a second sensor placed in a different position from said first sensor for detecting a flaw, and being arranged movably and rotatably against the end face;
    a driver means for driving said sensor head to cause said first sensor to move relative to the end face along a first and a second straight line, said first and said second straight lines pass through the center hole and cross with each other and to cause said second sensor to rotate in a circumferential direction around the center hole;
    an arithmetic means for obtaining an intersecting point of the first and the second straight lines responsive to a signal level obtained by said first sensor when said sensor head moves along the first straight line, and for determining the center of the end face based on a signal level obtained by said first sensor when said sensor head moves along the second straight line;
    a control means for controlling said driver means responsive to an output from said arithmetic means to rotate said sensor head when said first sensor is located at the center of the end face and said sensor head is in contact with the end face; and
    a flaw detecting means for detecting a flaw of the axle with said second sensor while said sensor head is rotated.

2. The apparatus according to claim 1, wherein said flaw detecting means sets gradually narrowing flaw detecting gates, and wherein at each set of said flaw detecting gates, a maximum echo is detected by said second sensor in order to obtain the position of a flaw which produces the maximum echo.

3. The apparatus according to claim 1, wherein said axle is that of an electric rail-car, said first sensor is an ultrasonic probe, said second sensor includes a vertical probe and an oblique probe, wherein a third sensor is provided and said third sensor is a displacement sensor.

4. The apparatus according to claim 2, wherein said second sensor is located at a position corresponding to an axle fitting hole, said axle fitting hole having a center, wherein said arithmetic means further comprises a means for obtaining the center of the axle fitting hole from a received signal level obtained by said second sensor when said sensor head is rotated and passes over said axle fitting hole while said first sensor is located at the sensor of the end face and said sensor head is in contact with the end face of the axle, and wherein said control means controls said driver means in response to an output of said arithmetic means.

5. The apparatus according to claim 4, wherein said axle is that of an electric rail-car, said first sensor is an ultrasonic probe, said second sensor includes a vertical and an oblique probe, wherein a third sensor is provided, and said third sensor is a displacement sensor.

6. The apparatus according to claim 2, wherein an indicator positioned relative to the center hole and an axle fitting hole to represent axle information is provided on the end face of the axle, wherein a third sensor is provided for detecting the indicator at a position corresponding to the indicator wherein said arithmetic means further comprises (1) a means for detecting the indicator based on an output from said third sensor while said sensor head is rotated and (2) a means for obtaining a true origin of the axle fitting hole from the positions of the center of the axle fitting hole and the indicator, and wherein said control means controls said driver means in response to an output from said arithmetic means.

7. The apparatus according to claim 6, wherein said axle is that of an electric rail-car, said first sensor is an ultrasonic probe, said second sensor includes a vertical and an oblique probe, wherein a third sensor is provided, and said third sensor is a displacement sensor.

8. A flaw detecting apparatus for non-destructively detecting a flaw in an axle, the axle having an endface which has a center hole, the flaw detecting apparatus comprising:
   a sensor head including a first sensor which detects a center of the endface and a second sensor placed in a different position from said first sensor which detects a flaw, and being arranged movably and rotatably against the endface;
   a drive mechanism which drives said sensor head to cause said first sensor to move relative to the endface along a first and a second straight line, said first and second straight lines pass through the center hole and cross with each other and to cause said second sensor to rotate in a circumferential direction around the center hole;
   an arithmetic unit which obtains an intersecting point of the first and second straight lines responsive to a signal level obtained by said first sensor when said sensor head moves along the first straight line, and which obtains the center of the endface based on a signal level obtained by said first sensor when said sensor head moves along the second straight line;
   a control unit which controls said driver mechanism and being responsive to an output from said arithmetic unit to rotate said sensor head when said first sensor is located at the center of the endface and said sensor head is in contact with the endface; and
   a flaw detecting unit which detects a flaw of the axle with said second sensor while said sensor head is rotated.

9. The apparatus according to claim 8, wherein said flaw detecting unit sets gradually narrowing flaw detecting gates, and wherein at each set of said flaw detecting gates, a maximum echo is detected by said second sensor in order to obtain the position of a flaw which produces the maximum echo.

10. The apparatus according to claim 8, wherein said axle is that of an electric rail-car, said first sensor is an ultrasonic probe, said second sensor includes a vertical probe and an oblique probe; and a third sensor, said third sensor is a displacement sensor.

11. The apparatus according to claim 9, wherein said second sensor is located at a position corresponding to an axle fitting hole, said axle fitting hole having a center, wherein said arithmetic unit further obtains the center of the axle fitting hole from a received signal level obtained by said second sensor when said sensor head is rotated and passes over said axle fitting hole while said first sensor is located at the center of the endface and said sensor head is in contact with the endface of the axle, and wherein said control unit controls the driver mechanism in response to an output from the arithmetic unit.

12. The apparatus according to claim 11, wherein said axle is that of an electric rail-car, said first sensor is an ultrasonic probe, said second sensor includes a vertical probe and an oblique probe and a third sensor, said third sensor is a displacement sensor.

13. The apparatus according to claim 9, wherein an indicator positioned relative to the center hole and an axle fitting hole to represent axle information is provided on the endface of the axle, wherein a third sensor is provided for detecting the indicator; wherein said arithmetic unit further includes a detector which detects the indicator based on an output from said third sensor while said sensor head is rotated and a unit for obtaining a true origin of the axle fitting hole from the positions of the center of axle fitting hole and the indicator, and wherein said control unit controls said driver mechanism in response to an output from said arithmetic unit.

14. The apparatus according to claim 13, wherein said axle is that of an electric rail-car, said first sensor is an ultrasonic probe, said second sensor includes a vertical probe and an oblique probe; and a third sensor, said third sensor is a displacement sensor.

15. A method for detecting a flaw in an axle having an endface and at least one reference location, the flaw detecting device having a sensor head disposed proximate to an endface and having a plurality of sensor heads; the method comprising the device implemented steps of:
   moving a first sensor in said sensor head along a first and a second straight line along the endface of the axle, said first and second straight lines crossing each other,
   determining the intersecting point between the first and second straight lines responsive to a signal level obtained by the first sensor when the first sensor moves along the first straight line,
   determining a center of the endface responsive to a signal level obtained by the first sensor when the first sensor moves along the second straight line,
   detecting a reference location on the endface of the axle responsive to a signal level obtained by a second sensor when the second sensor revolves around the first sensor,
   using the position of the reference location and the position of the center of the endface to detect a flaw.

16. A method as recited in claim 15, wherein the step for determining the intersecting point further includes moving a probe head along a line across the endface of the axle, obtaining a echo from said probe, determining when an echo amplitude falls below a predetermined decision level to obtain the location of the center point.

* * * * *